US008669293B2

(12) United States Patent
Levy et al.

(10) Patent No.: US 8,669,293 B2
(45) Date of Patent: *Mar. 11, 2014

(54) METHOD AND COMPOSITIONS FOR PREVENTING HORMONE INDUCED ADVERSE EFFECTS

(75) Inventors: Joseph Levy, Omer (IL); Yoav Sharoni, Omer (IL)

(73) Assignee: Lycored Ltd., Beer Sheva (IL)

( * ) Notice: Subject to any disclaimer, the term of this patent is extended or adjusted under 35 U.S.C. 154(b) by 970 days.

This patent is subject to a terminal disclaimer.

(21) Appl. No.: 10/240,090

(22) PCT Filed: Mar. 28, 2001

(86) PCT No.: PCT/IL01/00291
§ 371 (c)(1),
(2), (4) Date: Feb. 14, 2003

(87) PCT Pub. No.: WO01/78701
PCT Pub. Date: Oct. 25, 2001

(65) Prior Publication Data
US 2003/0148946 A1 Aug. 7, 2003

(30) Foreign Application Priority Data

Mar. 29, 2000 (IL) .......................................... 135335

(51) Int. Cl.
*A01N 31/04* (2006.01)
*A61K 31/07* (2006.01)
(52) U.S. Cl.
USPC ........................................................ 514/725
(58) Field of Classification Search
USPC .................... 514/12, 171, 763, 725
See application file for complete search history.

(56) References Cited

U.S. PATENT DOCUMENTS

| | | | |
|---|---|---|---|
| 3,833,350 A * | 9/1974 | Cooke et al. ................... | 504/326 |
| 5,422,119 A * | 6/1995 | Casper ........................... | 424/449 |
| 5,424,331 A | 6/1995 | Shlyankevich | |
| 5,475,006 A | 12/1995 | Burton et al. | |
| 5,516,528 A | 5/1996 | Hughes et al. | |
| 5,807,586 A | 9/1998 | Jackson et al. | |
| 5,827,900 A | 10/1998 | Levy et al. | |
| 5,830,887 A | 11/1998 | Kelly | |
| 5,834,044 A | 11/1998 | Schmitz et al. | |
| 5,904,924 A | 5/1999 | Gaynor et al. | |
| 6,132,790 A | 10/2000 | Schlipalius | |
| 6,218,436 B1 | 4/2001 | Howard et al. | |

FOREIGN PATENT DOCUMENTS

| | | |
|---|---|---|
| EP | 0 600 544 A1 | 6/1994 |
| WO | WO 00/61130 A1 | 10/2000 |
| WO | WO 01/26668 A1 | 4/2001 |

OTHER PUBLICATIONS

Adlercreutz, et al, "Plasma Concentrations of Phyto-Oestrogens in Japanese Men". (Nov. 13, 1993). Lancet. 342(8881)1209-10. Abstract.
Chan, et al, "Plasma Insulin-Like Growth Factor-I and Prostate Cancer Risk: A Prospective Study". (Jan. 23, 1998). Science. 279:563-566.
Constaninou, et al, "Genistein Induces Maturation of Cultured Human Breast Cancer Cells and Prevents Tumor Growth in Nude Mice[1-3]". (1998). Am J Clin Nutr. 68(suppl):1426S-30S.
Ernster, et al, "Benefits and Risks of Menopausal Estrogen and/or Progestin Hormone Use". (Mar. 1988). Prev Med. 17(2):201-23. Abstract.
Gooderham, et al, "A Soy Protein Isolate Rich in Genistein and Daidzein and Its Effects on Plasma Isoflavone Concentrations, Platelet Aggregation. Blood Lipids and Fatty Add Composition of Plasma Phospholipid in Normal Men". (Aug. 1996). J Nutr. 126(8):2000-6. Abstract.
Hankinson, et al, "Circulating Concentrations of Insulin-Like Growth Factor I and Risk of Breast Cancer". (May 9, 1998) Lancet. 351(9113):1393-1396. Abstract.
Karas, et al, "Lycopene Interferes with cell cycle progression and insulin-like growth factor I signaling in Mammary Cancer Cells". (Jan. 2000). Nutrition and Cancer. 36(1):101-111. Abstract.
King, R., "A Discussion of the Role of Oestrogen and Progestin in Human Mammary Carcinogenesis". (Nov. 1991). The Journal of Steroid Biochemistry and Molecular Biology. 39(5): 811-818. Abstract.
LeBail et al, "Estrogenic and Antiproliferative Activities on MCF-7 Huamn Breast Cancer Cells by Flavonoids". (Aug. 14, 1998). Cancer Letters. 130(1-2):209-216. Abstract.
Le Roith, et al, "Molecular and cellular aspects of the insulin-like growth factor I Receptor". Apr. 1995). Endocrine Reviews. 16(2):143-163.
Lobo, R., "The Role of Progestins in Hormone Replacement Therapy". (Jun. 1992). Am J Obstet Gynecol. 166(6 Pt 2):1997-2004. Abstract.

(Continued)

*Primary Examiner* — Yong Chong
(74) *Attorney, Agent, or Firm* — Browdy and Neimark, PLLC (57) ABSTRACT

A method for preventing the adverse effects which may he associated with the administration of at least one hormone to a subject without detectable cancer comprising administering to such subject at least one carotenoid. The method of the instant invention can be utilized to prevent a variety of adverse effects associated with the administration of hormones, including for example, an increased risk for developing cancer. The instantly claimed method prevents such adverse effects without inhibiting the beneficial activity of the hormone. Further provided by the present invention are compositions which are useful for preventing the adverse effects associated with the administration of hormones. The compositions of the instant invention may be in unit dosage form suitable for daily administration to a human.

16 Claims, 6 Drawing Sheets

(56) References Cited

OTHER PUBLICATIONS

Nishino, H., "Cancer Prevention by Carotenoids". (Jun. 18, 1998). Mutat Res. 402(1-2):159-163. Abstract.

Omenn, et al, "Effects of a combination of beta carotene and vitamin a on lung cancer and cardiovascular disease". (May 2, 1996). The new England journal of Medicine. 334(18)1150-1155.

Peto, et al, "Can Dietary Beta-carotene Materially Reduce Human Cancer Rates?". (Mar. 19, 1981). Nature. 290(5803):201-8. Abstract.

Staffa, et al, "Progestins and Breast Cancer. An Epidemiologic Review". (Mar. 1992). Fertil Steril. 57(3):473-491. Abstract.

Tanaka, et al, "Chemoprevention of Rat Oral Carcinogenesis by Naturally Occurring Xanthphylls, Astaxanthin and Canthaxanthin". (1995). Cancer Research. 55(18):4059-064. Abstract.

Tanaka, et al, "Suppression of Azoxymethane-Induced Rat Colon Carcinogenesis by Dietary Administration of Naturally Occurring Xanthophylls Astaxanthin and Canthaxanthin During The Postinitiation Phase". (1995). Carcinogenesis. 16(12):2957-2963. Abstract.

Wang, et al, "Phystoestrogen Concentration Determines Effects on DNA Synthesis in Human Breast Cancer Cells", (1997). Nutrition and Cancer. 28(3):236-247.

Klotz, Diane et al., "Activation of a Uterine Insulin-like Frowth Factor I Signaling Pathway by Clinical and Environment Estrogens: Requirement of Estrogen Receptor-$\alpha$" Endocrinology, vol. 141, No. 9 Sep. 2000, pp. 3430-3439.

Wang, Chuanfeng and Mindy Kurzer, "Phytoestrogen Concentration Determines Effects on DNA Synthesis in Human Breast Cancer Cells" Nutrition and Cancer, 28(3), 1997, pp. 236-247.

Kleinman, Dita et al "Modulation of Insulin-like Growth Factor I (IGF-I) Receptors and Membrane-Associated IGF-binding Proteins in Endometrial Cancer Cells by Estradiol" Endocrinology vol. 136, No. 6, 1995, pp. 2531-2537.

Sharoni, Yoav and Joseph Levy, "Anticarcinogenic Properties of Lycopene" Special Publication—Royal Society of Chemistry, Royal Society of Chemistry, London, GB, vol. 181, 1996, pp. 378-385.

Vaneenwyk, Juliet, et al "Dietary and Serum Carotenoids and Cervical Intraepithelial Neoplasia" International Journal of Cancer, vol. 48, No. 1, 1991, pp. 34-38.

Lutein Information Bureau, Protective Breast Cancer Effect From Carotene and Lutein/Zeaxanthin. 1996. Electronic Lutein Studies and Breast Cancer. [online], [retrieved on Jan. 2, 2003]. Retrieved from the Internet <URL:hhtp://www.luteininfo.com>.

Sightings. Soy Phytoestrogens—They Can Actually Promote Cancer. Dec. 7, 1999. [online]. [Retrieved on Jan. 2, 2003]. Retrieved from the Internet ,URL:http://www.sightings.com>.

Academy Health. Carotenoid Complex x 30—Quest. [retrieved on Jan. 2, 2003]. Retrieved from Internet <URL:http://www.ishop.co.uk/ishop/934/shopscr132.html>.

Healthy Origins®. Lyc-O-Mato Natural Tomato Lycopene. Product Brochure. [retrieved on Jan. 2, 2003]. Retrieved from Internet <URL:http://w3ww.healthyorigins.com/lycomato.htm>.

Freudenheim, Jo. et al, "Premenopausal Breast Cancer Risk and Intake of Vegetables, Fruits, and Related Nutrients", Journal of the National Cancer Institute, vol. 88, No. 6, Mar. 20, 1996. pp. 340-348.

Singh, Diljeet and Scott Lippman, "Cancer Chemoprevention Part 1: Retinoids and Carotenoids and Other Classic Antioxidants", Oncology, vol. 12, No. 11, Nov. 1998, [25 pp.].

United States Department of Agriculture Agricutural Research Service. ARS National Programs. National Program Annual Report: FY 1998. [online]. [retrieved on Jan. 9, 2003]. Retrieved from Internet <URL:http://nps.ars.usda.gov/documents/_doc.htm?npnumber=107&docid=231&cg_id=26 . . . >.

Wilson, Jean. "Hormones and Hormone Action", Harrison's Principles of Internal Medicine. 1991 part 12: Endocrinology and Metabolism, 12$^{th}$ Edition. pp. 1647-1652.

\* cited by examiner

Fig. 1

ECC-1 endometrial cancer

MCF-7 mammary cancer

Fig. 2

A. Hormone dependent-MCF-7   B. Hormone Independent-MDA-231

METHOD AND COMPOSITIONS FOR PREVENTING HORMONE INDUCED ADVERSE EFFECTS

FIELD OF THE INVENTION

The present invention provides a method and compositions for preventing adverse effects associated with the administration of hormones such as phytoestrogens and steroidal estrogens.

BACKGROUND OF THE INVENTION

Hormone intake by humans can occur through, inter alia, consumption of pharmaceutical compositions, foodstuffs, nutritional supplements, and nutraceuticals. Such hormones include phytoestrogens, or nonsteroidal estrogens, steroidal estrogens and progestins. Phytoestrogens comprise, for example, genistein, daidzein and glycitein, and their respective glucoside, malonylglucoside and acetylglucoside derivatives. Estrogens and progestins are known to be used for hormone replacement therapy (HRT) and in contraceptive medications. HRT with estrogens or with estrogen/progestin combinations has been the standard method for treating symptoms associated with menopause (Ernster V L et al. (1988) Benefits and Risks of Menopausal Estrogen and/or Progestin Hormone Use, Prev. Med. 17:201-223). The onset of menopause in mature adult women, which is accompanied by reduced estrogen production, is associated with an array of symptoms. These symptoms include hot and cold flashes, palpitations, dizziness, headaches, altered secretions as well as weight loss and gain. Reduced levels of circulating estrogen in post-menopausal women are also associated with increased risks of osteoporosis and coronary heart disease. Treatment protocols using estrogen alone significantly reduce the risks of cardiovascular disease and osteoporosis, if treatment begins at menopause. The protective effect of estrogen against heart disease is related to its ability to raise levels of circulating HDL and lower levels of LDL.

In contrast with this beneficial effect, long-term use of estrogens is positively correlated with an increased risk for endometrial cancer development. This risk may be reduced by simultaneous administration of a progestin, which prevents overgrowth of endometrial cells. Hence, an estrogen/progestin combined HRT protocol is recommended for a woman with an intact uterus. This form of combination therapy however, apparently diminishes the beneficial effects of estrogen on the plasma lipid profile (Lobo R. 1992. The Role of Progestins in Hormone Replacement Therapy; Am. J Obstet. Gynecol. 166:1997-2004). Furthermore, some progestins are associated with an increased risk of mammary cancer development (Staffa J. A. et al. 1991. Progestins and Breast Cancer: An Epidemiologic Review, 57: 473-491; King R. J. B. 1991. A Discussion of the Roles of Estrogen and Progestin in Human Mammary Carcinogenesis, *J. Ster. Biochem. Molec. Bio.* 39:8111-8118).

As disclosed in U.S. Pat. No. 5,516,528, HRT formulations have been developed which include phytoestrogens such as the soy-derived isoflavones genistein and daidzein. The health benefits of these plant products was first suggested by epidemiologic data indicating that Asian populations in which soy is a dietary staple suffer relatively low incidences of breast, uterine and other hormone-dependent cancers, ostensibly due to a high intake of soy and soy-derived products.

Although soy isoflavones have been shown to exert anti-proliferative effects in human adenocarcinoma and breast cancer cell lines in vitro, these effects occur only at relatively high, i.e. 15 molar ("M") concentrations (Constantinou, A. I. et al. 1998. Genistin Induces Maturation of Cultured Human Breast Cancer Cells and Prevents Tumor Growth in Nude Mice, Am. J. Clin. Nutr. 68:1426s-1430s; Le Bail, J. C. et al 1998. Estrogenic and Antiproliferative Activities on MCF-7 Human Breast Cancer Cells by Flavenoids, Cancer Lett. 130: 209-216). The anti-proliferative effects on cancer cells in vitro caused by phytoestrogens at such high concentrations may not have clinical relevance because the IC50 values are at least one order of magnitude greater than the blood concentrations achievable from soy-based diets.

A phytoestrogen concentration range of approximately 0.1 to 10 µM is representative of that found in healthy humans, both Asian and European, with soy-based diets. (Adlercreutz, H. et al. 1993. Plasma Concentrations of Phyto-oestrogens in Japanese Men, Lancet 342:1209-1210; Gooderham et al., 1996. A Soy Protein Isolate Rich in Genistein and Daidzein and its Effects on Plasma Isoflavone Concentrations, Platelet Aggregation, Blood Lipids and Fatty Acid Composition of Plasma Phospholipid in Normal Men, J. Nutr. 125:2000-2006). At these lower concentrations, various phytoestrogens, including genistein, counestrol, biochanin A, apigenin, luiolin, kaempferl and enterolactone, were shown to induce cell proliferation in estrogen receptor-positive, but not in estrogen receptor negative human breast cancer cell lines, thus demonstrating the estrogenic effects of these compounds (Wang, C. and Kurtzer, M. S. 1997. Phytoestrogen concentration Determines Effects on DNA synthesis in Human Breast Cancer Cells, Nutr. Cancer 28:236-247).

Hence, although phytoestrogens have been disclosed as beneficial components for HRT formulations, it has been found that the presence of phytoestrogens at levels normally found in healthy humans increases the risk for development of hormone-dependent cancers.

The carotenoid astaxanthin has been demonstrated to have anti-tumorigenic effects in vivo in rodent models (Tanaka, T. et al. 1995. Suppression of azoxymethane-induced rat colon carcinogenesis by dietary administration of naturally occurring xanthophylls astaxanthin and canthaxanthin during the postinitiation phase. Carcinogenesis 16: 2957-2963; Tanaka, T. et al. 1995. Chemoprevention of rat oral carcinogenesis by naturally occurring xanthophylls, astxanthin and canthaxanthin. Canc. Res. 55:4059-4064).

The carotenoid phytoene has also demonstrated anti-cancer activity. The cancer preventive activity of phytoene was demonstrated following introduction of the gene encoding phytoene synthase into mammalian cells normally lacking this gene. These cells acquired resistance against malignant transformation imposed by transfection of activated oncogenes (Nishino, H. 1998. Cancer prevention by carotenoids. Mutat. Res. 402:159-163).

β-carotene was the first carotenoid suggested to have anti-cancer properties (Peto et al. 1981. Carotenoids and cancer: an update with emphasis on human intervention studies, Nature 290:201-208). Epidemiological studies of β-carotene's effect on cancer, however, have produced conflicting results. Although some studies have showed that β-carotene increases the risk for developing cancer (Omenn et al., 1996. Effects of a combination of beta-carotene and vitamin A on lung cancer and cardiovascular disease, N. Engl. J. Med 334: 1150-1155), other cell culture and animal studies have indicated quite consistently that β-carotene has an anti-carcinogenic effect.

Lycopene, a carotenoid found in tomatoes, is strongly associated with anti-oxidant and anti-cancer activities. The anti-proliferative effects of lycopene on breast cancer cells in vitro has been shown to be mediated through interference with the IGF-1 receptor signaling pathway and cell cycle progression (Karas et al. 2000. Lycopene interferes with cell cycle progression and insulin-like growth factor I signaling in mammary cancer cells. Nutr. Cancer, 36:101-11). IGF-I is a growth factor obligatory for malignant transformation of breast tissue, and its concentration in plasma determines risk factor for cancers of both the breast (LeRoith, D., Werner, H., Beitner-Johnson, D. and Roberts, C. T., Jr. 1995. Molecular and cellular aspects of the insulin-like growth factor I receptor. Endocr. Rev. 16:143-59; Hankison S. E. et al. 1998. Circulating concentrations of insulin-like growth factor-I and risk of breast cancer. Lancet 351:1393-6) and prostate (Chan, J. M., Stampfer, M. J. Giovannucci, E., Gann, P. H., Ma, J. 1998 Plasma insulin-like growth factor-I and prostate cancer risk: a prospective study. Science 279:563-66).

U.S. Pat. No. 5,827,900 discloses the use of lycopene for inhibiting the growth of cancers in vitro and in vivo, including hormone-dependent endometrial and breast cancers. U.S. Pat. No. 5,827,900 requires very high carotenoid dosage levels. The '900 patent discloses 7 mg/Kg to 20 mg/Kg per day as illustrative lycopene dosages. The method of the '900 patent would thus require 490 mg-1400 mg of lycopene per day for a person weighing 70 kg (154 lbs.).

The combination of lycopene and soy isoflavones in dietary supplements has been disclosed in U.S. Pat. No. 5,904,924. The '924 patent discloses a nutritional powder composition comprising soy isoflavones (phytoestrogens) and lycopene. The '924 patent only refers to the ability of phytoestrogens to decrease the risk of estrogen dependent cancers. Nowhere does the '924 patent disclose that dietary intake of phytoestrogens incurs a risk for adverse health affects, and that such risk can be reduced by the concomitant consumption of carotenoids.

The use of phytoestrogens in dietary supplements has been disclosed in U.S. Pat. Nos. 5,830,887 and 5,807,586. The combination of carotenoid mixtures, vitamin A and phytoestrogens in dietary supplements for women was disclosed in U.S. Pat. No. 5,807,586. The dosage amounts of vitamin A and mixed carotenoids disclosed in the '586 patent range from about 400 to about 2000 µg retinol equivalents ("RE"). 1 RE is equivalent to about 6 µg beta-carotene and about 12 µg alpha-carotene or cryptoxanthin. The dosage range disclosed in the '586 patent is thus approximately equivalent to about 2.4-12 mg of beta-carotene and about 4.8-24 mg of alpha-carotene or cryptoxanthin. Since lycopene and lutein do not exhibit substantial provitamin A activity, the RE for these carotenoids cannot be calculated. The dosage levels disclosed in the '586 patent, however, are expressed only in RE units. The disclosure of the '586 patent thus does not limit dosage levels of carotenoids which do not exhibit substantial provitamin A activity, such as lycopene and lutein.

The instant invention is directed to a method and compositions useful for preventing adverse effects which may be associated with the intake of pharmaceutical compositions, foodstuffs, nutritional supplements, or nutraceuticals comprising hormones such as estrogens, phytoestrogens and progestins. Such adverse effects include, but are not limited to, the increased risk of various types of cancer. The administration of phytoestrogens has been previously disclosed as beneficial in decreasing the risks for developing cancer. It has been found, however, that intake of phytoestrogens can incur an increased risk for developing hormone-dependent cancers.

There is thus a long felt need for a method and a composition useful for preventing the adverse effects which may be associated with the intake of foodstuffs, pharmaceutical compositions, nutritional supplements, and nutraceuticals comprising phytoestrogens, steroidal estrogens, and/or progestins. A need also exists for compositions which can be used to prevent the adverse effects associated with the administration of pharmaceutical compositions containing hormones such as, for example, steroidal estrogens and progestins, without inhibiting the beneficial activity of such hormones.

It is therefore a purpose of the present invention to provide a method for inhibiting the adverse effects which may be associated with the consumption of food stuff or dietary supplements comprising phytoestrogens and progestins.

It is another purpose of the present invention to provide a composition useful for preventing the adverse effects which may be associated with the consumption of food stuff or dietary supplements comprising phytoestrogens and progestins.

It is yet a further purpose of the present invention to provide a novel hormone-comprising pharmaceutical composition with reduced side effects relating to adverse effects that the hormones may have, thus overcoming the disadvantages of the pharmaceutical composition known from the prior art.

Other objects of the invention will become apparent as the description proceeds.

SUMMARY OF THE INVENTION

The present invention provides a method for preventing the adverse effects which may be associated with the administration of at least one hormone to a subject without detectable cancer comprising administering to such subject at least one carotenoid. The method of the instant invention can be utilized to prevent a variety of adverse effects associated with the administration of hormones, including, for example, an increased risk for developing cancer. The instantly claimed method prevents such adverse effects without inhibiting the beneficial activity of the hormone.

Accordingly, an object of the instant method is to prevent the adverse effects associated with administration of estrogen and/or progestin in hormone replacement therapy without inhibiting the beneficial activity of such hormone.

Another object of the present invention is to provide a method for preventing the adverse effects associated with the administration of phytoestrogens. It is yet another object of the presently claimed method to prevent adverse effects associated with the administration of phytoestrogens without inhibiting the beneficial activity of such hormone.

Further provided by the present invention are compositions which are useful for preventing the adverse effects associated with the administration of hormones. The compositions of the instant invention may be in unit dosage form suitable for once daily administration to a human.

An object of the instant invention is to provide compositions for preventing adverse effects associated with the administration of phytoestrogens.

A further object of the present invention is to provide compositions for preventing adverse effects associated with the administration of steroidal hormones or progestins.

Yet another object of the instant invention is to provide compositions that are useful for preventing adverse effects associated with the administration of phytoestrogens, steroidal hormones or progestins, and that do not inhibit the beneficial activity of such hormones.

DETAILED DESCRIPTION OF A PREFERRED EMBODIMENT OF THE INVENTION

The following description is illustrative of preferred embodiments of the invention. The following description is not to be construed as limiting, it being understood that the skilled person may carry out many obvious variations to the invention.

As used throughout this specification, "hormone" refers to steroidal estrogens, progestins, and nonsteroid estrogens (phytoestrogens) derived from higher plants, as well as chemically modified derivatives, synthetic equivalents, and mixtures thereof.

As used throughout this specification, "steroidal estrogen" or "estrogen" refers to estradiol, estrone, estriol, synthetic equivalents, chemically modified derivatives, and mixtures thereof.

As used throughout this specification, "progestin" refers to agents that cause progesterone effects, such as, for example, progesterone, medroxyprogesterone, norethindrone, norethisterone, norgestrel, synthetic equivalents, chemically modified derivatives, and mixtures thereof.

As used throughout this specification, "phytoestrogen" refers to soy protein isoflavones, flavones, as well as the glucoside, malonylglucoside and acetylglucoside derivatives, synthetic equivalents, chemically modified derivatives, and mixtures thereof. Illustrative phytoestrogens include, for example, daidzein, genistein, and glycitein.

As used throughout this specification, "administration" or "administering" refers to the introduction to a subject by one or more of various routes, including oral ingestion, dermal, vaginal, intrauterine, intramuscular or intravenous injection.

Carotenoids useful for the instant invention comprise, but are not limited to, lycopene, alpha-carotene, beta-carotene, zeta-carotene, phytoene, phytofluene, lutein, zeaxanthin, cryptoxanthin astaxantine, and mixtures thereof. The carotenoids referred to throughout the specification are from natural or synthetic sources or from genetically modified organisms.

The present invention provides a method for preventing the adverse effects which may be associated with the administration of at least one hormone to a subject without detectable cancer comprising administering to such subject at least one carotenoid in an amount effective to prevent such adverse effects. The carotenoid can be administered in a composition separate from the hormone or in a composition further comprising the hormone.

A single carotenoid as well as combinations and mixtures thereof can be administered in the method of the present invention. It has surprisingly been found that the various combinations of lycopene, phytoene and phytofluene demonstrate a beneficially synergistic effect in preventing the adverse effects associated with the administration of hormones. Accordingly, carotenoid mixtures of lycopene and phytoene; lycopene and phytofluene; and lycopene, phytoene, and phytofluene can be administered in the presently claimed method.

Figure 1:
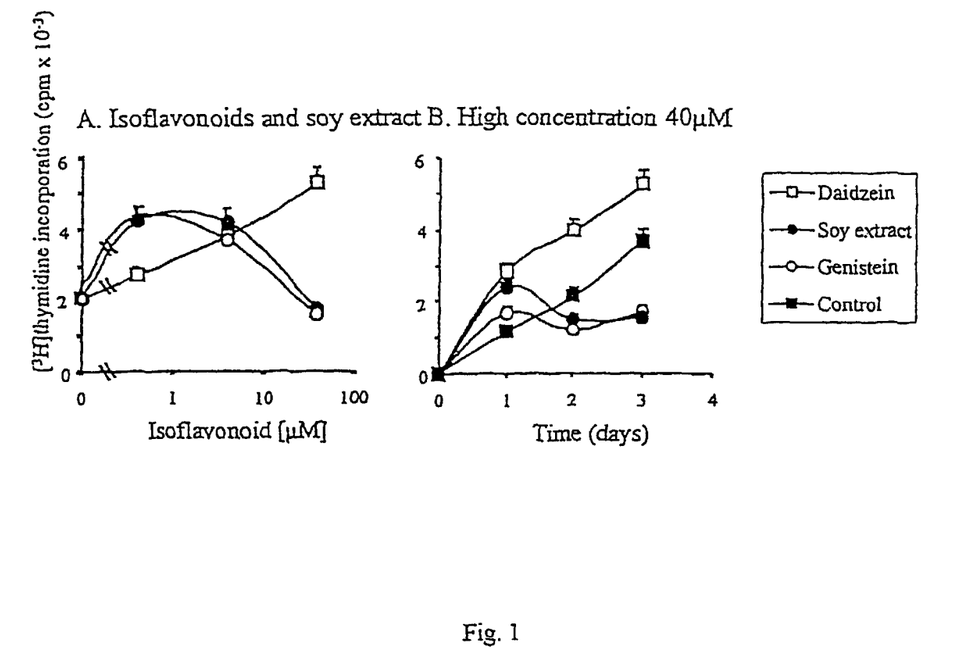
FIG. 1—Stimulation of ECC-1 endometrial cancer cell proliferation by isoflavenoids and soy extract.

Upon consuming phytoestrogen-containing products, the physiological concentration of these phytoestrogens in the subject's blood serum can reach levels of 0.4 to 4 µM. FIG. 1 panel A demonstrates that incubation of ECC-1 endometrial cancer cells in the presence of the phytoestrogens genistein or daidzein, or a mixture of the two as occurs in soy extract, at such a concentration range, induces a significant increase in cell proliferation rate (indicated by cpm, counts per minute). Hence, subjects who reach these phytoestrogen concentrations increase their risk of certain types of cancer, inter alia, endometrial and mammary cancer.

Figure 2:
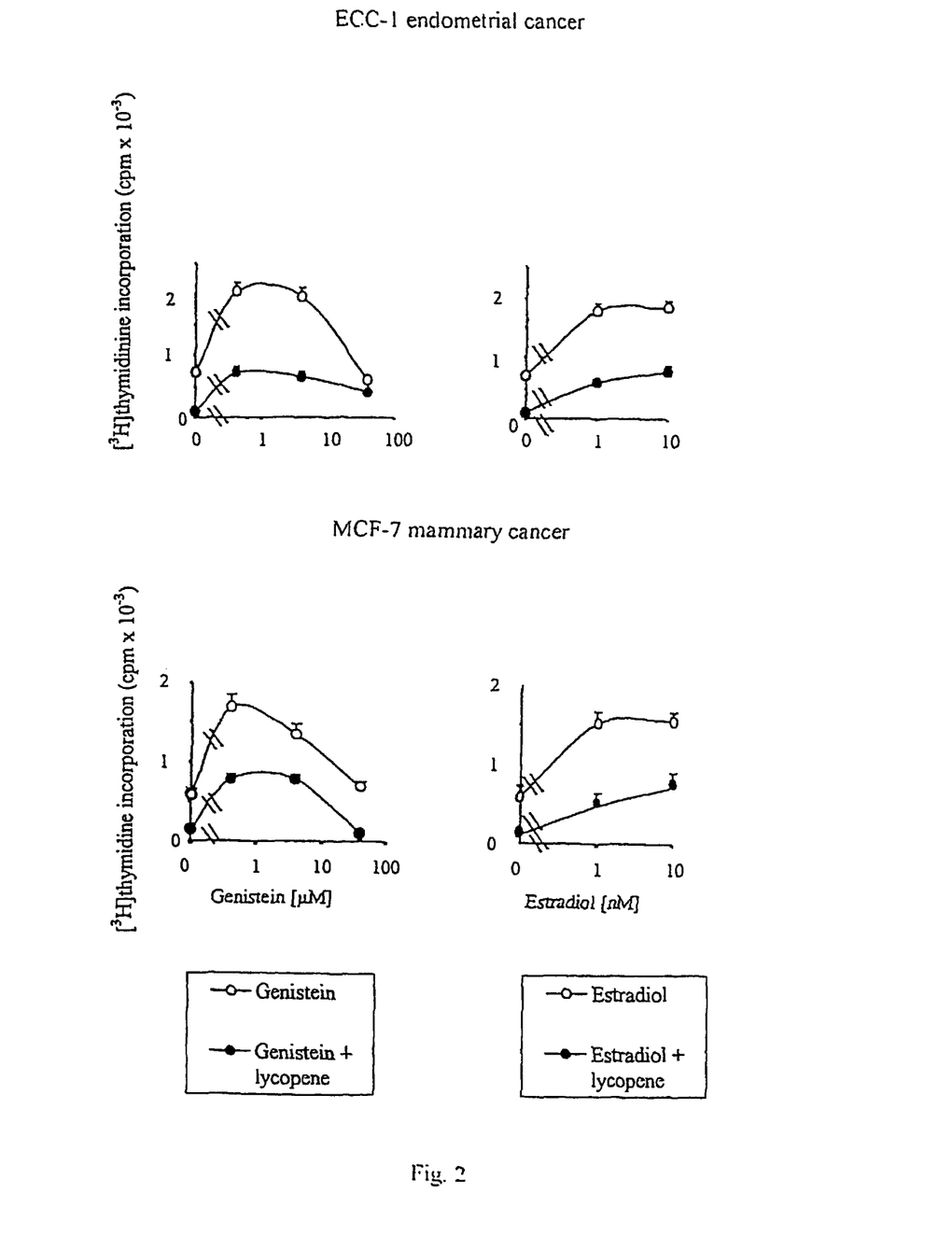
FIG. 2—Lycopene inhibits both genistein- and estradiol-induced stimulation of hormone dependent malignant cells.
Figure 4:
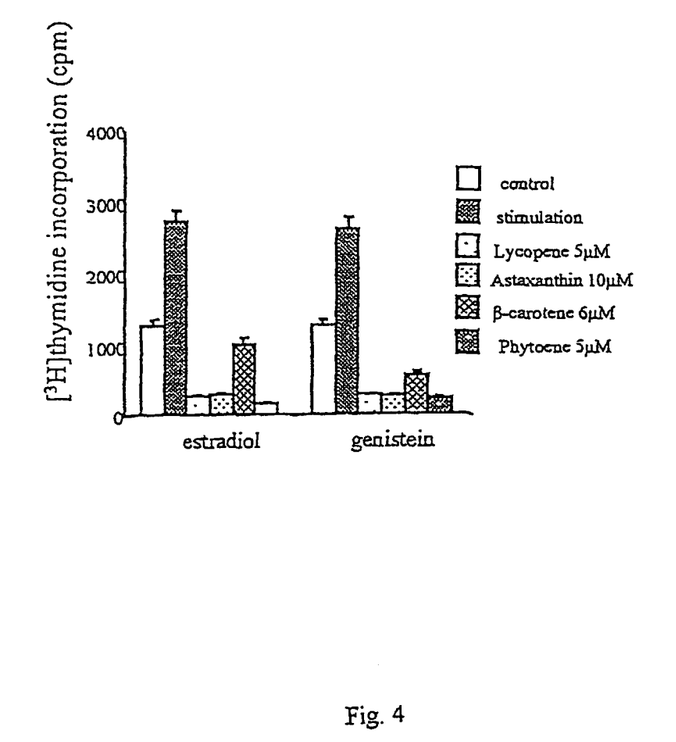
FIG. 4—Various carotenoids inhibit estradiol- and genistein-induced proliferation of ECC-1 endometrial cancer cells.

FIG. 2 demonstrates this effect by comparing the cell proliferation rate of cancer cells incubated in the presence of increasing concentrations of the phytoestrogen genistein and estradiol both in the presence and absence of lycopene. It is clearly shown that the increased rate of cell proliferation induced by genistein is substantially inhibited by the presence of lycopene. The same effect is seen in both endometrial cancer cells (FIG. 2, upper graphs) and mammary cancer cells (FIG. 2, lower graphs). This inhibiting effect is further demonstrated in FIG. 4 where it can be clearly seen that not only lycopene, but also carotenoids such as astaxanthin, phytoene and beta-carotene are effective inhibitors of the cell proliferation induced by the phytoestrogen genistein.

Physiological concentrations of phytoestrogens to levels greater than about 10 µM can occur immediately following consumption of foodstuffs or dietary supplements comprising phytoestrogens. Such levels are greater than 0.4 to 4 µM, which is the steady state physiological concentration range of phytoestrogens in humans who have consumed phytoestrogens. FIG. 1, panel B demonstrates that such transiently high concentrations of phytoestrogens can induce cell proliferation and thus increase the risk for cancer. FIG. 1, panel B demonstrates that incubation of ECC-1 endometrial cancer cells with 40 µM daidzein or genistein, or a mixture of the two as occurs in soy extract, significantly increases cell proliferation within the first day in culture. The inhibitory effect of the phytoestrogens was significant only from the second day of incubation. The methods of the present invention operate to prevent the adverse effects of such elevated phytoestrogen levels which can occur immediately subsequent to consumption of phytoestrogen-containing products or compositions.

According to an embodiment of the invention, the adverse effects associated with the administration of at least one phytoestrogen to a subject without detectable cancer are prevented by co-administering at least one carotenoid in an amount effective to prevent such adverse effects. The method of the present invention encompasses preventing such adverse effects without inhibiting the beneficial activity of said phytoestrogens.

The carotenoid is administered in an amount from about 2 mg to about 10 mg per day, preferably from about 2 mg to about 6 mg per day, most preferably about 2 mg per day. Carotenoids that do not exhibit substantial provitamin A activity such as, for example, zeta-carotene, phytoene, phytofluene, lutein, zeaxanthin, astaxantine, and lycopene, are preferably administered in an amount of about 2 mg per day.

Where the method of the instant invention comprises administering to a subject at least one carotenoid selected from the group consisting of alpha-carotene, beta-carotene, and cryptoxanthin, said carotenoid is preferably administered in an amount of about 2 mg per day.

The method of the present invention can also be utilized to prevent adverse effects associated with the administration of hormones such as estrogen and progestin to a subject without detectable cancer. Such method can be used, for example, in hormone replacement therapy, whereby the hormone is co-administered with at least one carotenoid in an amount sufficient to prevent adverse effects associated with the administration of such hormone. The carotenoid can be administered in a composition separate from such hormone or in a composition further comprising such hormone.

The presently claimed method is particularly helpful for hormone replacement therapy. Hormone replacement therapy with estrogen alone, or estrogen replacement therapy, can incur a risk for developing endometrial cancer. In an attempt to reduce this risk, hormone replacement therapy comprising of a combined estrogen/progestin administration is often utilized. This form of therapy, however, can diminish the beneficial effects of estrogen. Furthermore, some progestins are associated with an increased risk for developing mammary cancer. The method of the instant invention can prevent the adverse effects associated with the administration of estrogen and progestin, and can do so without inhibition of the beneficial activity of such hormones as occurs in conventional hormone replacement therapy. In another embodiment, the method of the present invention is used to prevent the additive adverse effects caused by elevated levels of IGF-1. IGF-1 occurs naturally in the serum of normal, healthy individuals. The occurrence of IGF-1 at elevated levels, however, constitutes a significant risk factor for cancers of the breast and prostate. The risk for developing cancer associated with the administration of hormones is thus increased in an individual who has elevated IGF-1 levels. The additive adverse effects caused by a combination of elevated IGP-1 levels and consumption of hormones are prevented by administering at least one carotenoid in an amount sufficient to prevent such adverse effects.

In yet another embodiment, the method of the instant invention is utilized to prevent the adverse effects associated with elevated levels of IGF-1 in the absence of hormones. The presence of IGF-1 at elevated levels constitutes a significant risk factor for certain cancers even in the absence of hormones. These adverse effects, including increasing the risk for developing cancer, which are caused by elevated IGF-1 levels can be prevented by administering at least one carotenoid in an amount sufficient to prevent such adverse effects.

The present invention provides compositions useful for preventing adverse effects associated with the administration of hormones. Such adverse effects include, for example, an increased risk for the development of cancer. The compositions of the instant invention are in a unit dosage form suitable for administration to a human. The compositions comprise a physiologically effective amount of at least one hormone and at least one carotenoid in an amount effective to prevent such adverse effects. The instantly claimed compositions can prevent the adverse effects associated with the administration of hormones without inhibiting the beneficial activity of such hormones.

A single carotenoid as well as combinations and mixtures thereof can be used in the compositions of the present invention. It has surprisingly been found that various combinations of lycopene, phytoene and phytofluene demonstrate a beneficially synergistic effect in preventing the adverse effects associated with the administration of hormones. Accordingly, carotenoid mixtures of lycopene and phytoene; lycopene and phytofluene; and lycopene, phytoene, and phytofluene can be used in the presently claimed compositions. When administering such a mixture, a mixture of lycopene and phytoene is preferred.

The compositions of the present invention operate to prevent the adverse effects of elevated phytoestrogen levels which can occur immediately subsequent to consumption of phytoestrogen-containing products or compositions (see FIGS. 1 and 2).

Co-administering at least one carotenoid to a phytoestrogen-consuming subject in an amount of about 2 mg per day attenuates the risk for cancer which is associated with the consumption of phytoestrogens. The present invention encompasses a unit dosage form suitable for once daily administration to a human comprising a physiologically effective amount of at least one phytoestrogen and at least one carotenoid, preferably in an amount of about 2 mg. Preferably, the carotenoid is in an amount sufficient to cause effective serum concentrations of said carotenoid of up to about 1.5 µM.

Where the composition of the present invention comprises at least one phytoestrogen, the carotenoid is preferably one which does not exhibit substantial provitamin A activity. Carotenoids which do not exhibit substantial provitamin A activity include, for example, lycopene, zeta-carotene, phytoene, phytofluene, lutein, zeaxanthin, and astaxantine. Where the carotenoid comprises a mixture of carotenoids, such mixture preferably comprises lycopene and phytofluene; more preferably lycopene, phytofluene, and phytoene; most preferably lycopene and phytoene.

A further embodiment of the instant invention is a unit dosage form suitable for once daily administration to a human comprising a physiologically effective amount of at least one hormone selected from the group consisting of steroidal estrogen, estradiol, estrone. medroxyprogesterone, norethindrone, norethisterone, progestin, norgestrel, and progesterone, and at least one carotenoid present in an amount effective to prevent the adverse effects which may result from the administration of such hormone. This unit dosage form can prevent the adverse effects associated with the administration of such hormones without inhibiting the beneficial activity of such hormones. Preferably, the carotenoid is in an amount from about 2 to about 10 mg, more preferably from about 2 to about 6 mg, most preferably about 2 mg. Preferably, the carotenoid is an amount sufficient to cause effective serum concentrations of said carotenoid of up to about 1.5 µM. Where the carotenoid comprises a mixture of carotenoids, such mixture preferably comprises lycopene phytoene and phytofluene; more preferably lycopene, phytofluene, and phytoene.

The instantly claimed compositions that comprise at least one steroidal estrogen or progestin are particularly helpful for hormone replacement therapies used to treat menopause in women. Conventional hormone replacement therapies used to treat menopause can increase the risk for developing certain cancers. The compositions of the present invention can be used in hormone replacement therapies, while also preventing adverse effects such as the risk for developing cancer which can be associated with the administration of steroidal estrogens or progestins. The presently claimed compositions can prevent such adverse effects without inhibiting the beneficial activity of the hormones.

Figure 3:
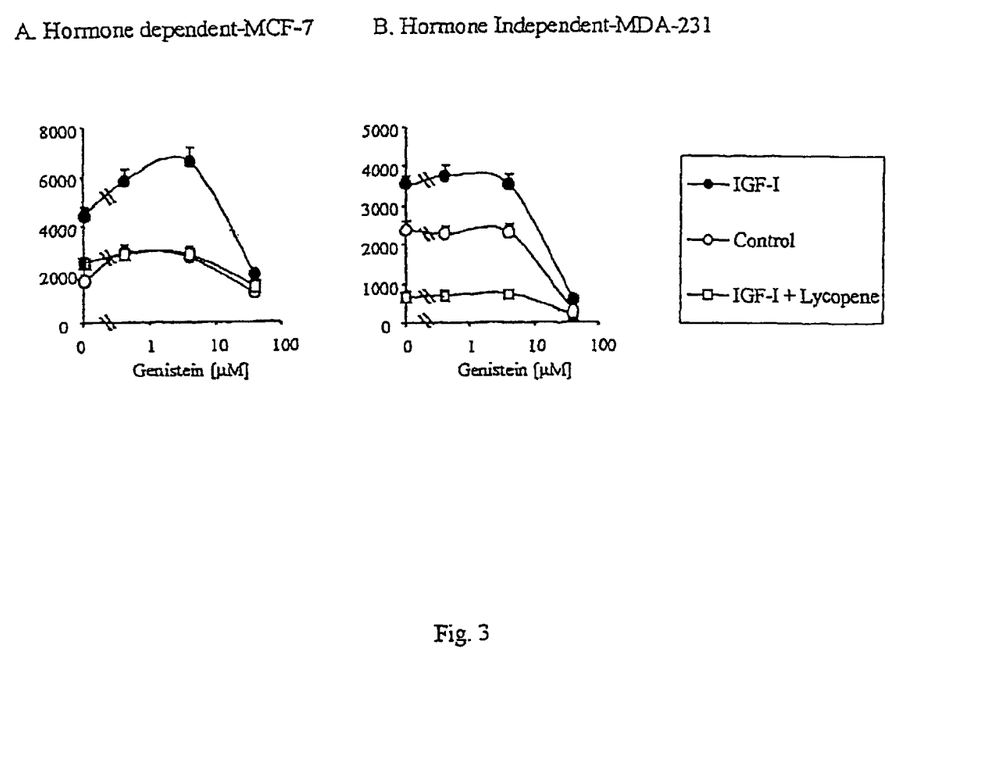
FIG. 3—Effect of lycopene on mammary cancer cells cultured in the presence of genistein and IGF-1.

The compositions of the present invention can be used to prevent the additive adverse effects on cell proliferation incurred by elevated levels of the growth factor IGF-1 hormone intake in the presence of phytoestrogens. IGF-1 occurs naturally in the serum of normal individuals, but its occurrence at elevated levels significantly increases the risk for developing cancers of the breast and prostate. FIG. 3 panel A demonstrates that incubation of hormone dependent MCF-7 mammary cancer cells with both genistein (in the range from about 0.4 to 4 µM and IGF-1 (30 nM) significantly increases the cell proliferation rate, as compared to control cultures stimulated only with genistein. Addition of lycopene in the range of 3 to 5 µM inhibits the cell proliferation stimulated by the combined presence of IGF-1 and genistein. Accordingly, a composition of the instant invention comprising at least one phytoestrogen and at least one carotenoid, can be administered to a subject with elevated IGF-1 levels in order to prevent the additive adverse affects caused by such elevated IGF-1 levels.

The present invention will now be further explained in the following examples, which Further describe, but do not limit the scope of the invention.

EXAMPLES

General Procedures
Carotenoid Sources and Solutions

Lycopene (≥97%) was extracted from 5% tomato oleoresin as in U.S. Pat. No. 5,827,900. Synthetic lycopene was purchased from Sigma Chemical Co. (Israel), as was astaxanthin and beta-carotene. Phytoene was extracted from tomato extract at Lycored Natural Products Industries Ltd, Beer Sheva, Israel.

Tetrahydrofuran (THF) containing 0.25% butylated hydroxytoluene was added to purified carotenoids as an antioxidant. Carotenoids were dissolved in THF at a concentration of 2 mM and stored at −70° C. Immediately before use, stock solutions were thawed and added to the cell culture medium under nitrogen, followed by vigorous stirring. Precipitates formed were removed by filtration through Millex-HV filter (Millipore). Final carotenoid concentrations in the medium were determined by spectrophotometry after extraction in 2-propanol and n-hexane:dichloronomethane, as in U.S. Pat. No. 5,827,900.

The final THF concentration of 0.5% did not have any significant effect on the measured parameters. All procedures were carried out under dim lighting.

Hormones Growth Factors and Other Cell Culture Materials

Estradiol, genistein and daidzein were purchased from Sigma Chemical Co. (Israel). Soy extract containing 15% genistein, 15% daidzein and 1% glycitein was purchased from Kikkoman, (Chiba-ken, Japan). Human recombinant IGF-1 was purchased from GroPep, (Adelaide, Australia). Dulbecco's modified Eagle's medium (DMEM), fetal calf serum (FCS) and $Ca^{2+}/Mg^{2+}$-free phosphate buffered saline (PBS) were purchased from Biological Industries (Beth Haemek, Israel).

Cell Lines

The human endometrial cancer (estrogen dependent) cell line ECC-1 was developed by Dr. P. G. Satyaswaroop, Pennsylvania State University, PA, U.S.A, and generously provided to us by Dr. R. Oregan, Norwestern University, Chicago, Ill., U.S.A. Human mammary cancer cell lines MCF-7 (estrogen dependent) and MDA-231 (hormone independent) were obtained from the American Type Culture Collection (Rockville, Md., U.S.A.).

Cell Culture and Cell Proliferation Assay

Cells were cultured in DMEM containing penicillin (100 U/ml), streptomycin (0.1 mg/ml)) nystatin (12.5 µg/ml), insulin (0.6 µg/ml), and 10% FCS. Cells were stripped of endogenous steroids according to the procedure of Vignon et al. (1987, Biochem. Biophys. Res. Comm., 146:1502-8) by successive passages in medium without phenol red containing 10% and then 3% of charcoal-stripped FCS. Cells were seeded into 96 multiwell plates (5,000 cells per well) in DMEM containing 3% of charcoal-stripped FCS. After one day the medium was changed to one containing the solubilized carotenoid or THF alone. The medium was changed daily to ensure a continuous supply of carotenoid.

After incubation, the number of cells and the rate of cell proliferation were estimated by the incorporation of [$^3$H] thymidine incorporation into cellular DNA, as described in U.S. Pat. No. 5,827,900. Cell growth was also measured by direct cell counting with a Coulter counter after trypsinization and dilution in Isotone-II (Coulter Electronics, Luton, England). A good correlation was found between the two methods.

Example 1

Stimulation of ECC-1 Endometrial Cancer Cell Proliferation By Isoflavonoids.

ECC-1 cells were incubated with increasing concentrations of the isoflavones genistein and daidzein, the two primary isoflavones in soy products, and with soy extract. Cell proliferation after three days was measured by [$^3$H]thymidine incorporation into DNA (FIG. 1, panel A). Genistein, daidzein and soy extract all stimulated cell proliferation at 0.4 and 4 µM concentrations, which are in the ranges found in the plasma of soy supplemented individuals. At higher, non-physiological concentrations (≥10 µM), genistein and soy extract but not daidzein, inhibited cell proliferation after three days in culture (FIG. 1, panel A). These results demonstrate that genistein has biphasic effects on endometrial cancer cell growth, while daidzein is only stimulatory.

ECC-1 cells were also incubated with a single high concentration (40 µM) of each of genistein, daidzein and soy extract and cell proliferation was assayed daily over the course of three days. The results, presented in FIG. 1, panel B show that after one day of incubation this high isoflavone concentration also stimulated cell proliferation, while inhibitory effects of genistein were seen only by the second day in culture. These results suggests that transiently elevated levels of isoflavones, particularily genistein, to levels normally associated with cell growth inhibition, may in fact be stimulatory in soy supplemented individuals.

Example 2

Lycopene Inhibits Both Genistein and Estradiol Stimulation of Hormone-Dependent Malignant Cells.

The comparative effects of estradiol and genistein supplementation on the proliferation of the hormone-dependent cell lines MCF-7 mammary cancer and ECC-1 endometrial cancer were examined (FIG. 2). In each of these cell lines, genistein exhibited biphasic effects on proliferation, stimulating at low concentrations and inhibiting at high concentrations (FIG. 2), as demonstrated in Example 1. Estradiol at each of the concentrations tested (1 and 10 nM) was only stimulatory for cell growth (FIG. 2). These results suggest that the stimulatory effect of genistein may be due to its estrogenic action.

Cell cultures stimulated either by genistein or estradiol, as described above, were further supplemented with lycopene and assayed for cell proliferation after three days in culture. As shown in FIG. 2, lycopene supplementation at 3 to 5 µM significantly inhibited both basal growth and estrogen-induced (either genistein or estradiol) growth in both of the hormone-dependent cancer cell lines tested.

Example 3

Lycopene Inhibits IGF-1-Stimulated Growth In Hormone-Dependent and Hormone-Independent Mammary Cancer Cells.

FIG. 3 shows that IGF-1 (30 nM supplementation of both hormone-dependent MCF-7 mammary cancer cells (panel A) and hormone-independent MDA-231 mammary cancer cells (panel B) significantly stimulates cell growth. In MCF-7 cells, the stimulatory effect of genistein is further augmented in the presence of IGF-I (FIG. 3, panel A). MDA-231 is stimulated by IGF-I, but not by genistein. Thus genistein not only stimulates hormone-dependent cancer cell proliferation, but IGF-I as well as other growth factors further augment this effect.

Cell cultures supplemented as above were further supplemented with lycopene at 3 to 5 µM concentration. As shown in FIG. 3, lycopene inhibits IGF stimulation in both hormone-dependent and hormone-independent mammary cancer cell lines. In the case of MDA-231 cells, cell proliferation was reduced to levels less than that of controls.

Example 4

Various Carotenoids Inhibit Estradiol and Genistein Induced Proliferation of ECC-1 Cells.

The ECC-1 hormone-dependent cell line was stimulated either by estradiol (10 nM, FIG. 4) or by genistein (1 µM, FIG. 4) and test cultures were additionally supplemented with various carotenoids. The results clearly demonstrate that all carotenoids tested (lycopene, beta-carotene, astaxanthin and a mixture of phytoene and phytofluene) effectively inhibited both estradiol- and genistein-induced cell proliferation.

Example 5

Lycopene Inhibits in a Dose Dependent Manner Estradiol and Genistein Induced Proliferation of ECC-1 Endometrial Cancer Cells.

Figure 5:
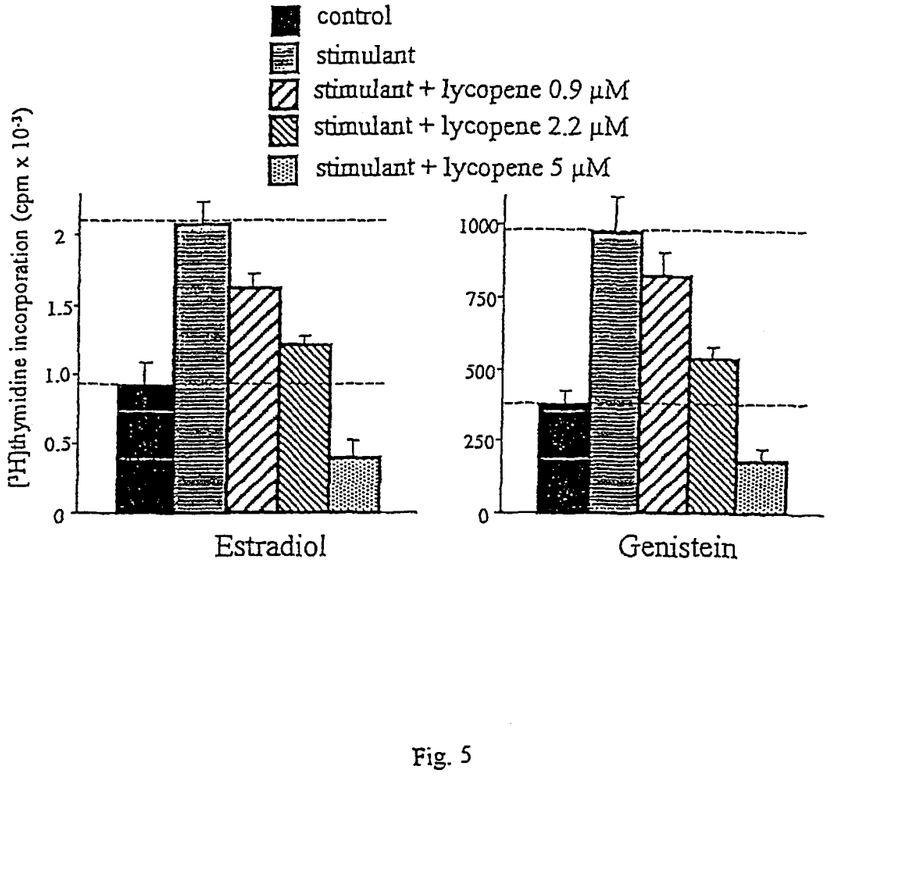
FIG. 5.—Lycopene inhibits in a dose dependent manner estradiol- and genistein-induced proliferation of ECC-1 endometrial cancer cells.

The hormone-dependent endometrial cancer cell line ECC-1 was stimulated either by estradiol (10 nM, FIG. 5) or by genistein (1 µM, FIG. 5) and test cultures were additionally supplemented with various concentrations of lycopene. The results clearly demonstrate that while increasing lycopene concentration resulted in greater inhibition, all lycopene concentrations tested were effective in inhibiting both estradiol- and genistein-induced cell proliferation. The lowest lycopene concentration tested (0.9 µM) is in the physiological range found in human serum.

Example 6

Figure 6:
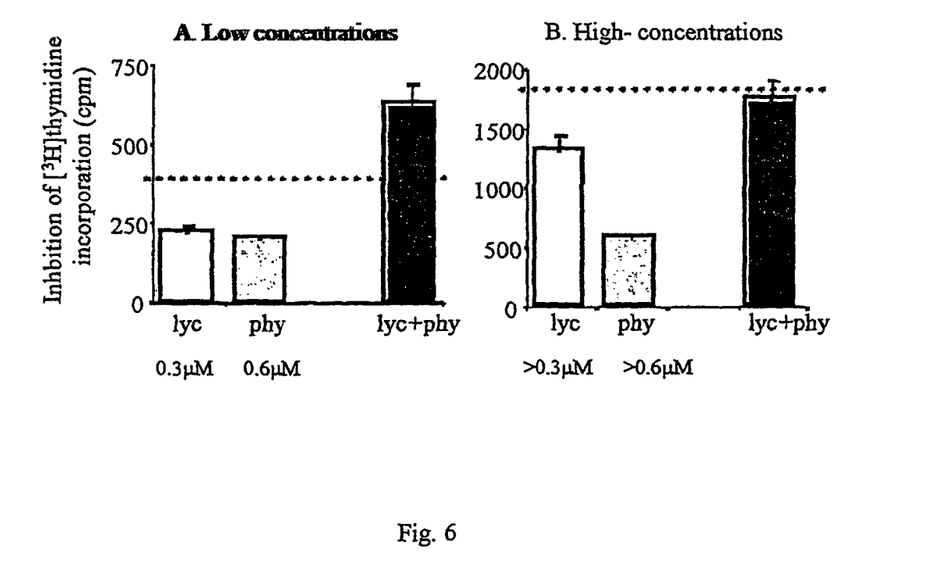
FIG. 6.—Combined effect of lycopene and phytoene on genistein-induced proliferation of ECC cells.

MCF-7 mammary cancer cells were stimulated by genistein (4 µM) and test cultures were additionally supplemented with lycopene or phytoene or a combination of both, at either physiological concentrations (FIG. 6 panel A) or at about one order of magnitude greater than the physiological concentrations (FIG. 6 panel B). The results demonstrate that high, non-physiological concentrations of the individual carotenoids were effective in significantly inhibiting phytoestrogen-induced cell proliferation, and the combination of the two was even more effective(FIG. 6 panel B). At lower physiological concentrations, lycopene was only marginally effective in inhibiting phytoestrogen-induced cell proliferation, and phytoene was not effective. The combination of lycopene and phytoene however, at physiological concentrations, was effective in significantly inhibiting phytoestrogen-induced cell proliferation.

While embodiments of the invention have been described by way of illustration, it will be apparent that the invention may be carried out with many modifications, variations and adaptations, without departing from its spirit or exceeding the scope of the claims.

The invention claimed is:

1. A method for reducing the risk of the development of a hormone-associated cancer in a female subject undergoing hormone replacement therapy, consisting essentially of:
    (i) administering to said subject a hormone selected from the group consisting of natural steroidal estrogens, progestins, and nonsteroidal estrogens (phytoestrogens) derived from higher plants, as well as synthetic analogs thereof, and mixtures thereof; and
    (ii) administering to said subject a mixture of cartenoids comprising phytoene and consisting of at least one additional carotenoid selected from the group consisting of lycopene and phytofluene,
    wherein said mixture of cartenoids is administered in an amount sufficient to prevent in said subject an increase in cell proliferation rate which would otherwise be stimulated by the hormone replacement therapy.

2. The method of claim 1, wherein said administering of said hormone is by oral ingestion, dermal, vaginal, intrauterine, intramuscular or intravenous injection.

3. The method of claim 1, wherein said administering of said carotenoid is by oral ingestion, dermal, vaginal, intrauterine, intramuscular or intravenous injection.

4. The method of claim 1, wherein the hormone is co-administered with the carotenoid.

5. The method of claim 1, wherein the carotenoid is administered in a composition separate from the hormone.

6. The method of claim 1, wherein the carotenoid is administered in a composition comprising the hormone.

7. The method of claim 1, wherein the hormone is a steroidal estrogen selected from the group consisting of estradiol, estrone, estriol and mixtures thereof.

8. The method of claim 1, wherein the hormone is a progestin selected from the group consisting of progererstone, medroxyprogesterone, norethindrone, norethisterone, norgestrel, synthetic equivalents, chemically modified derivatives, and mixtures thereof.

9. The method of claim 1, wherein the hormone is a phytoestrogen selected from the group consisting of soy protein isoflavones, flavones, as well as the glucoside, malonylglucoside and acetylglucoside derivatives, synthetic equivalents, chemically modified derivatives, and mixtures thereof.

10. The method of claim 1, wherein the hormone is a phytoestrogen selected from the group consisting of daidzein, genistein, and glycitein.

11. The method of claims 1, wherein the mixture of carotenoids comprises both lycopene and phytoene.

12. The method of claim 1, wherein the mixture of carotenoids comprises lycopene, phytoene and phytofluene.

13. The method of claim 1, wherein the carotenoid is administered in an amount of about 2 mg to about 10 mg per day, thereby producing a serum concentration of the carotenoid of up to 1.5 µM.

14. The method of claim 1, wherein the carotenoid is administered in an amount of about 2 mg to about 6 mg per day.

15. The method of claim 1, wherein the carotenoid is administered in an amount of about 2 mg per day.

16. The method of claim 1 wherein the hormone-associated cancer is endometrial or mammary cancer, and the female subject undergoing hormone replacement therapy is a female at risk of development of endometrial or mammary cancer.

* * * * *